(12) United States Patent
Multhoff (10) Patent No.: US 7,722,863 B2
(45) Date of Patent: May 25, 2010

(54) USE OF GRANZYME B AS AN HSP70/HSP70 PEPTIDE DEPENDENT INDUCER OF APOPTOSIS IN TUMOR CELLS

(75) Inventor: Gabriele Multhoff, München (DE)

(73) Assignee: Multimmune GmbH, Munich (DE)

( * ) Notice: Subject to any disclaimer, the term of this patent is extended or adjusted under 35 U.S.C. 154(b) by 24 days.

(21) Appl. No.: 10/526,586

(22) PCT Filed: Aug. 22, 2003

(86) PCT No.: PCT/EP03/09341

§ 371 (c)(1),
(2), (4) Date: Dec. 12, 2005

(87) PCT Pub. No.: WO2004/018002

PCT Pub. Date: Mar. 4, 2004

(65) Prior Publication Data

US 2006/0111285 A1    May 25, 2006

(30) Foreign Application Priority Data

Aug. 23, 2002  (EP) .................... 020182846

(51) Int. Cl.
*A61K 38/43* (2006.01)
(52) U.S. Cl. .................................... 424/94.1
(58) Field of Classification Search ............ None
See application file for complete search history.

(56) References Cited

U.S. PATENT DOCUMENTS

| | | | | |
|---|---|---|---|---|
| 6,130,087 A | * | 10/2000 | Srivastava et al. | 435/372.3 |
| 6,261,839 B1 | * | 7/2001 | Multhoff et al. | 435/373 |
| 2003/0086919 A1 | * | 5/2003 | Rosenblum et al. | 424/94.63 |
| 2003/0186384 A1 | * | 10/2003 | Barth et al. | 435/69.5 |
| 2004/0014652 A1 | * | 1/2004 | Trouet et al. | 514/12 |

FOREIGN PATENT DOCUMENTS

| WO | WO 0191798 A2 | * | 12/2001 |
|---|---|---|---|
| WO | WO/02/22656 | * | 9/2002 |

OTHER PUBLICATIONS

Shi, L., Mai, S., Israels, S., Browne, K., Trapani J.A., and Greenberg A.H. (1997) Granzyme B (GraB) autonomously crosses the cell membrane and Perforin initiates apoptosis and GraB nuclear localization. Journal of Experimental Medicine, 185(5):855-866.*
Spaeny-Dekking, E.H.A., Hanna W.L., Wolbink A.M., Wever P.C., Kummer A.J., Swaak A.J.G., Middledorp J.M., Huisman J.G., responses in vitro and in vivo. Journal of Immunology 160:3610-3616.*
Wever P.C., Mulder J.B.G., Weening J.J., and ten Berge I.J.M., (1997) Immunocytochemical detection of Granzymes A and B in peripheral blood lymphocytes from healthy individuals after non-enzymateic antigen retrieval. Journal of Histochemistry & cytochemistry 45(3):467-469.*
M.S. Buzza and P.I. Bird. Biol. Chem. (2006) 387, pp. 827-837.*
J.A. Trapani and V.R. Sutton. Curr. Opion Immunol. (2003) 15, pp. 533-543.*
Pfister et al, "Patient Survival by Hsp70 Membrane Phenotype," American Cancer Society, 2007, pp. 926-935.

* cited by examiner

*Primary Examiner*—Andrew D Kosar
(74) *Attorney, Agent, or Firm*—Casimir Jones, S.C.

(57) ABSTRACT

The present invention relates to a method of inducing or enhancing the expression of granzyme B in natural killer (NK) cells. The present invention relates also to a use of said NK cells for the preparation of a pharmaceutical composition for the treatment of tumors, viral or bacterial infections or inflammatory diseases. Further, the present invention relates to the use of granzyme B for the treatment of tumors, viral or bacterial infections or inflammatory diseases, wherein the tumor cells or the cells affected by said infection or inflammation express Hsp70 in their cell surface.

8 Claims, 9 Drawing Sheets

Figure 1

B Identification of human granzyme B by MALDI-TOF analysis

| Coomassie stain | Mr observed | Mr expected | peptide start | peptide end | sequence |
|---|---|---|---|---|---|
| | 877.364 | 877.396 | 145 | 151 | MTVQEDR |
| | 893.369 | 893.391 | 145 | 151 | MTVQEDR |
| | 1048.572 | 1048.566 | 192 | 201 | VAGIVSYGR |
| | 1055.549 | 1077.556 | 136 | 144 | HSHTLQEVKV |
| | 1288.702 | 1288.703 | 73 | 83 | RPIPHPAYNPK |
| | 1442.722 | 1442.740 | 61 | 72 | EQEPTQQFIPVK |

Colo+

SEQUENCE LISTING

```
<160> NUMBER OF SEQ ID NOS: 6

<210> SEQ ID NO 1
<211> LENGTH: 14
<212> TYPE: PRT
<213> ORGANISM: Homo sapiens

<400> SEQUENCE: 1

Thr Lys Asp Asn Asn Leu Leu Gly Arg Phe Glu Leu Ser Gly
1               5                   10

<210> SEQ ID NO 2
<211> LENGTH: 7
<212> TYPE: PRT
<213> ORGANISM: Homo sapiens

<400> SEQUENCE: 2

Met Thr Val Gln Glu Asp Arg
1               5

<210> SEQ ID NO 3
<211> LENGTH: 9
<212> TYPE: PRT
<213> ORGANISM: Homo sapiens

<400> SEQUENCE: 3

Val Ala Gly Ile Val Ser Tyr Gly Arg
1               5

<210> SEQ ID NO 4
```

```
-continued

<211> LENGTH: 10
<212> TYPE: PRT
<213> ORGANISM: Homo sapiens

<400> SEQUENCE: 4

His Ser His Thr Leu Gln Glu Val Lys Val
1               5                   10

<210> SEQ ID NO 5
<211> LENGTH: 11
<212> TYPE: PRT
<213> ORGANISM: Homo sapiens

<400> SEQUENCE: 5

Arg Pro Ile Pro His Pro Ala Tyr Asn Pro Lys
1               5                   10

<210> SEQ ID NO 6
<211> LENGTH: 12
<212> TYPE: PRT
<213> ORGANISM: Homo sapiens

<400> SEQUENCE: 6

Glu Gln Glu Pro Thr Gln Gln Phe Ile Pro Val Lys
1               5                   10
```

USE OF GRANZYME B AS AN HSP70/HSP70 PEPTIDE DEPENDENT INDUCER OF APOPTOSIS IN TUMOR CELLS

The present invention relates to a method of inducing or enhancing the expression of granzyme B in natural killer (NK) cells. The present invention relates also to a use of said NK cells for the preparation of a pharmaceutical composition for the treatment of tumors, viral or bacterial infections or inflammatory diseases. Further, the present invention relates to the use of granzyme B for the treatment of tumors, viral or bacterial infections or inflammatory diseases, wherein the tumor cells or the cells affected by said infection or inflammation express Hsp70 on their cell surface.

A variety of documents is cited throughout this specification. The disclosure content of said documents is herewith incorporated by reference.

Elevated cytoplasmic levels of heat shock protein 70 (Hsp70) have been found to protect tumor cells against programmed cell death (Nylandsted et. al. (2000) Ann. N.Y. Acad. Sci. 926, 122). Hsp70 is the major stress inducible form of the heat shock protein family (HSP), which is primarily located in the cytosol. Evidence accumulated during recent years has demonstrated that extracellular localized and plasma membrane-bound HSPs are highly immunogenic and expose the cells to immune attack (Schild et. al. (1999) Current Opinion in Immunology 11, 109). Following receptor-mediated uptake (Arnold-Schild et. al. (1999) J. Immunol. 162, 3757) and re-presentation by antigen presenting cells (APC), HSP-chaperoned peptides elicit a cytotoxic, $CD8^+$ T cell response (Suto et. al. (1995) *Science* 269, 1585). Several receptors, including CD91 and toll-like receptors 2 and 4 (TLR2/4), have been identified that mediate interaction of HSP90 (gp96), HSP70 (Hsp70, Hsc70) and HSP60 peptide complexes with APCs (Basu et. al. (2001) Immunity 14, 303; Binder et. al. (2000) Nat. Immunol. 1, 151; Sondermann et. al. (2000) Biol. Chem. 381, 1165.; Ohashi et. al. (2000) J. Immunol. 164, 558). A peptide-independent "chaperokine effect" has been described for members of the HSP70 group. Binding of exogenous HSP70 to monocytes via TLR2/4 in a CD14 dependent pathway induces receptor clustering and the secretion of proinflammatory cytokines via MyD88/IRAK/NFκ-B signal transduction (Pfeiffer et. al. (2001) Eur. J. Immunol. 31, 3153; Asea et. al. (2000) Nature Medicine, 6, 435; Asea et. al. (2000) Cell Stress & Chaperones, 5, 425; Asea et. al. (2002) J Biol Chem. 277(17), 15028).

Natural killer (NK) cells have been found to specifically interact with a C-terminal localized epitope of Hsp70 (Botzler et. al. (1998) Cell Stress & Chaperones, 3, 6), that is presented on the cell membrane of tumor cells (Multhoff et. al. (1995) Int. J. Cancer, 61, 272; Multhoff et. al. (1997) J. Immunol. 158, 4341). The amount of membrane-bound Hsp70 on tumor cells positively correlates with the sensitivity to the lysis mediated by NK cells: Physical (heat) as well as chemical (cytostatic drugs) stress has been found to increase Hsp70 cell surface expression on tumor cells and thereby rendering them better targets for NK cells (Multhoff (1997) Int. J. Hyperthermia 13, 39; Botzler et. al. (1999) Exp. Hematol. 27, 470; Rabinovich et. al. (2000) J. Immunol. 165, 2390; Feng et. al. (2001) Blood 97, 3505). Incubation of purified NK cells with recombinant Hsp70-protein increases their cytolytic activity against Hsp70 membrane-positive tumor cells (Multhoff et. al. (1999) Exp. Hematology 27, 1627). The same effect is achieved by a 14 amino acid peptide, termed TKD (TKDNNLLGRFELSG (SEQ ID NO.1), aa450-463), derived from the C-terminal domain of Hsp70. This region corresponds to the domain of Hsp70 exposed to the extracellular milieu of viable tumor cells (Multhoff et. al. (2001) Cell Stress & Chaperones 6, 337). Concomitant with an increased cytolytic activity, following contact either with Hsp70-protein or with Hsp70-peptide TKD the cell surface expression of the activating form of the C-type lectin receptor CD94 was enhanced in NK cells. Blocking assays using an inhibitory antibody specific for CD94 revealed an involvement of CD94 in the interaction of NK cells with Hsp70 membrane-positive tumor cells (Multhoff et. al. (1999) Exp. Hematology 27, 1627). These data indicate that apart from HLA-E presenting leader peptides of classical HLA-alleles (Lanier et. al. (1998) Immunity 8, 693; Braud et. al. (1998) Nature 391, 795), the C-terminal localized Hsp70-peptide sequence TKD might be considered as a potential ligand for a yet undefined activating CD94 receptor complex. Although the preceding observations indicate that Hsp70-peptide functions as a tumor-selective target recognition structure for CD94 positive NK cells (Multhoff et al. (1997) J. Immunol. 158, 4341), the mechanism by which NK cells lyse Hsp70 positive tumor target cells remained to be elucidated. In addition, it is desirable to specifically trigger the lytic activity of NK cells towards tumor cells in a more specific manner than has hitherto been possible. All these scientific goals serve as a means to derive more efficacious and more specific approaches to disease treatment and in particular to tumor treatment.

Surface expression of heat-shock proteins including Hsp70 has been reported to occur also after viral infection or in response to stress. In particular, membrane Hsp70 was found in HIV-infected lymphoid cells (Di Cesare et al. (1992), Immunology 76, 341) and in HTLV I-infected rabbit cell lines (Chouchane et al. (1994), J. Infect. Dis. 169, 253). Similarly, it is conceivable that cells infected by bacteria or affected by inflammation express Hsp70 on their cell surface. Consequently, the lytic activity of NK cells or granzyme B can be directed towards cells infected by viruses or bacteria as well as towards cells affected by inflammation.

Thus, the technical problem underlying the present invention was to provide means and methods for a specific treatment of diseases and in particular of tumors, viral and bacterial infections and inflammatory diseases.

The solution to said technical problem is achieved by providing the embodiments characterized in the claims.

Accordingly, the present invention relates to a method of inducing or enhancing the expression of granzyme B in natural killer (NK) cells comprising contacting NK cells with (a) Hsp70 protein; (b) a (C-terminal) fragment of (a) comprising the amino acid sequence TKDNNLLGRFELSG (SEQ ID NO:1); (c) a (poly)peptide comprising the amino acid sequence TKDNNLLGRFELSG (SEQ ID NO:1); or (d) a combination of (a), (b) and/or (c).

Granzyme B is a serine protease well known in the art and is described to be involved in the process of apoptosis/programmed cell death (Berke (1995) Cell, 81(1), 9-12; Froelich et. al. (1998) Immunology Today, 19(1), 30-26); Metkar S et al. Cytotoxic cell granule-mediated apopstosis: perforin delivers granzyme B serglycin complexes into target cells without plasma membrane pore information, Immunity 16 (2002), 417-428

This enzyme promotes DNA fragmentation by cleavage of procaspases into their activated form and thereby induces programmed cell death through a Bcl-2 inhibitable pathway. Granzyme B starts to induce the process of apoptosis upon presence in the cytosol of a target cell.

The term "NK cells" ("natural killer cells") comprises large, granular lymphocytes expressing CD45 on the surface and exhibiting killer activity without prior stimulation. They are particularly characterised in that they do not express CD3 or T cell receptor α/β- or γ/δ and can be stimulated by interleukin-2.

The NK cells stimulated by the method of the invention are further characterised by the following properties:
- they are transient plastic-adherent after addition of IL-2 in amounts of 10 to 10,000 Units, e.g. of 100 I U, wherein IL-2 can be purchased from the firm Chiron;
- the adherence takes effect 3-18 hours after addition of IL-2 on newly isolated PBL (peripheral blood lymphocytes depleted-by monocytes);
- the NK cells exhibit a CD16dim expression (average value of fluorescence weak);
- the NK cells express CD56 and CD57 as typical NK marker;
- the NK cells express CD94 (C-type lectin killer cell receptor)
- the NK cells secrete after activation with Hsp70 and cytokines IFN gamma;
- the NK cells can be stimulated by addition of Hsp70, Hsp70 fragment or Hsp70-peptide (purified protein) (growth and cytotoxic activity);
- they are not dependent on the patient's MHC type.

According to the invention, other NK-cell populations can be used, too. Further methods for obtaining said population are known in the art and include isolation using magnetic beads and cell-sorting. In this case, however, it is a prerequisite that they can be activated by Hsp70 or by the above-mentioned fragments or (poly)peptides. According to the invention, isolated NK cells can be used. It is furthermore possible to use cell mixtures such as peripheral mononuclear blood cells (PBMC) containing NK cells.

In a particularly preferred embodiment of the method of the invention peripheral blood mononuclear cells (PBMC) or a fraction thereof which contain NK cells are L used as physiological cell suspensions.

Using appropriate methods, the NK cells can be obtained from the patients to be treated or from a healthy donor by taking blood. Preferably, buffy-coats or lymphocyte concentrates obtained by other means containing NK cells are to be used.

Buffy-coats or lymphocyte concentrates are taken from patients via the veins and e.g. heparin is added to prevent clotting of the cells. The buffy-coats to which heparin has been added are collected in a sterile receptacle (usually sterile plastic bags) and then centrifuged using Ficoll density centrifugation resulting in an accumulation of blood cells (=PBMC, peripheral blood mononuclear cells, e.g. lymphocytes, monocytes, granulocytes, and so on). The lymphocyte concentrate remains sterile in sterile culture bags.

The buffy-coats containing peripheral blood mononuclear cells are used in the form of a physiological cell suspension, preferably with heparin added. The heparin prevents aggregation of the cells.

Methods for the stimulation of NK cells by incubation with Hsp70 proteins of C-terminal fragments thereof have been described in WO 99 49 881. Surprisingly it has been found, that expression of granzyme B is induced or enhanced in NK cells by contacting said cells with Hsp70 protein, a fragment thereof comprising the amino acid sequence TKDNNLLGRFELSG (SEQ ID NO:1), a (poly)peptide comprising the amino acid sequence TKDNNLLGRFELSG (SEQ ID NO:1), or a combination of said proteins/(poly)peptides preferably in combination with IL-2. Preferably, the fragment referred to above and in connection with other (preferred) embodiments of the invention is a carboxy-terminal (C-terminal) fragment of Hsp70.

According to the invention, the term "Hsp70 protein" relates to eukaryotic heat-shock proteins (HSPs). The expression of said HSPs can be induced by heat but also by a number of other reagents such as e.g. amino acid analogues, heavy metals, ionophores or cytotoxines, wherein the factor of the increase in the expression by means of induction is at least 5, compared to the constitutive expression. The complete amino acid sequence has been published in Milner et al. (1990) Immunogenetics 32 (4), 242-251.

According to the invention, the term "fragment" of the Hsp70 protein also comprises (poly)peptides exhibiting an amino acid sequence from the range of amino acids 384-641 of the human Hsp70. All C-terminal (carboxy-terminal) fragments at least comprise the amino acid sequence TKDNNLLGRFELSG (SEQ ID NO: 1) Methods for the isolation of corresponding (poly)peptides are known in the art and particularly described in the appended example 1. Thus, the person skilled in the art is also able to produce fragments from the above-mentioned fragment 384-641 by recombinant techniques without further ado (standard methods for this are described in Sambrook et al., "Molecular Cloning, A Laboratory Manual", 2. edition 1989, CSH Press, Cold Spring Harbor, N.Y.) and test them for the activation properties wanted.

The term (poly)peptide refers to peptides as well as polypeptides (proteins). According to the conventional understanding, peptides comprise up to 30 amino acids whereas polypeptides consists of more than 30 amino acids. This convention is also employed in accordance with the invention. Further, in accordance with the invention, the amino acids throughout the description are referred to by the one letter code.

In one alternative (poly)peptides comprising the amino acid sequence TKDNNLLGRFELSG (SEQ ID NO:1) are (poly)peptides consisting of the recited amino acid sequence and optionally further amino acid stretches N-terminally and C-terminally thereof derived from Hsp70, fused to further randomly chosen or naturally occuring amino acid sequences. Thus, the method of the present invention relates to the stimulation of NK cells by fusion proteins comprising the sequence of the 14-mer Hsp70-peptide.

A preferred embodiment of the invention relates to a method wherein the Hsp70 protein, the (C-terminal) fragment thereof, the (poly)peptide comprising the amino acid sequence TKDNNLLGRFELSG (SEQ ID NO:1), or the combination thereof is in an uncomplexed state.

HSPs are known in the art to occur in complexes with a large number of different substrates peptides (Tamura et. al. (1997) Science, 278, 117-223). However, it has been suprisingly found that heat-shock proteins, (C-terminal) fragments thereof or derivatives derived therefrom (see above) induce immunological activities by means of activation of NK cells even if they do not form complexes with peptides.

Thus, according to the methods described in WO 99 49 881 the person skilled in the art is able stimulate NK cells using Hsp70 protein or (poly)peptide comprising the amino acid sequence TKDNNLLGRFELSG (SEQ ID NO:1) in an uncomplexed state.

According to a preferred embodiment the method of the invention is an in vivo Method.

A procedure envisaged would include to inject Hsp70, Hsp70 fragment or Hsp70 peptide into patents for in vivo stimulation of NK cells to produce granzyme B.

According to alternatively preferred embodiments said method is an ex vivo method or an in vitro method.

This method comprises isolation of NK cells or a population of cells comprising NK cells as described herein above, wherein a physiological cell suspension containing NK cells is mixed with Hsp70 protein, the C-terminal fragment thereof or a derivative thereof or a protein/(poly)peptide comprising the amino acid sequence TKDNNLLGRFELSG (SEQ ID NO:1) and incubated to induce or enhance expression of granzyme B in the NK cells.

The incubation can e.g. take place in an incubator, at physiological temperature (37° C.) on a shaker (gentle shaking), at 5% $CO_2$+>80% humified atmosphere also otherwise retaining physiological conditions that allow the survival of NK cells.

A further preferred embodiment of the invention relates to a method further comprising reinfusion of preferably autologous and/or allogeneic NK cells with induced or enhanced granzyme B expression into a mammal.

Once the NK cells have undergone an in vitro or ex vivo treatment to induce or enhance granzyme B expression, they are re-infused into a patient. Re-infusion can take effect using standard medical equipment. For example, reinfusion of NK cells or PBMC containing NK cells can be i.v., i.p., s.c., or intratumoral.

According to a further preferred embodiment of the invention said mammal is a human.

In another preferred embodiment of the method of the invention said contacting of the NK cells with Hsp70 protein, the (C-terminal) fragment thereof or a derivative thereof or a protein/(poly)peptide comprising the amino acid sequence TKDNNLLGRFELSG (SEQ ID NO:1) is effected for at least 12 hours. According to a further preferred embodiment said contacting is effected for at least 4 days.

The present invention relates in another preferred embodiment to a method wherein said NK cells, prior to said contacting, are obtained from bone marrow cells by incubating said bone marrow cells with interleukin-15 (IL-15) and stem cell factor (SCF) at concentrations of 1 ng/ml-1000 ng/ml per cytokine for at least 7 days up to 4 months.

This preferred embodiment of the invention allows for the fresh isolation of NK cells after stimulation of bone marrow cells with the named cytokines. The NK cells such obtained display the typical NK cell markers referred to herein above. Preferred concentration of cytokines are in the range of 100 ng/ml for each cytokine. After stimulation with the cytokines and differentiation into NK cells which display CD94 and CD56 on their surface, contacting of these cells may proceed with Hsp70 protein or the above mentioned fragment of (poly)peptide or the combination of the above as mentioned herein before.

An alternative embodiment of the invention relates to the use of NK cells which produce (i.e. express) granzyme B after stimulation with (a) Hsp70 protein; (b) a (C-terminal) fragment of (a) comprising the amino acid sequence TKDNNLLGRFELSG (SEO ID NO:1); (c) a (poly)peptide comprising the amino acid sequence TKDNNLLGRFELSG (SEO ID NO:1); or (d) a combination of (a), (b) and/or (c); for the preparation of a pharmaceutical composition for the treatment of tumors, viral and bacterial infections and inflammatory diseases.

According to the invention, pharmaceutical preparations are defined as substances and preparations of substances which, when used on or in the human body, are meant for healing, alleviating, preventing or recognising diseases, ailments, physical defects or pathological discomforts.

Optionally, said pharmaceutical compositions further comprise a pharmaceutically acceptable carrier, diluent or adjuvant.

Examples of suitable pharmaceutically acceptable (tolerable) carriers are known to the person skilled in the art and comprise, for example, phosphate-buffered saline solutions, water, emulsions, such as oil/water emulsions, sterile solutions, and so on. The pharmaceutical compositions (pharmaceutical preparations) containing such carriers may be prepared according to common methods. The pharmaceutical compositions may be administered to the respective individuals in an appropriate dosage. Ways of administration are, for example, intravenous (i.v.), intraperitoneal (i.p.), intratumoral, subcutaneous (s.c.), intramuscular (i.m.), topic or intradermal. The dosage depends on many factors, e.g. on the patient's size, sex, weight, age as well as the type of the composition specially administered, the kind of administration and so on. The compositions may be administered locally or systemically. Generally, administration is carried out parenterally. Therefore, the NK cells treated with Hsp70 protein, the C-terminal fragment thereof or a derivative thereof or a protein/(poly)peptide comprising the amino acid sequence TKDNNLLGRFELSG (SEO ID NO:1) according to the invention are preferably injected intravenously. An injection may also be carried out directly into the tumour with an effective amount of NK cells being injected. Other known types of application are, of course, also possible. An operable number of NK cells administered includes the range of $5 \times 10^7$ to $2 \times 10^9$ NK cells, for example, as components of a leukapheresate. In such a leukapheresate, NK cells are usually present in an amount of between 5% and 20%.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous, carriers include water, aqueous solutions, emulsions or suspensions, including saline such as 0.9% NaCl, phosphate buffered, X-vivo 20 etc. and buffered media. Parenteral vehicles include sodium chloride solution, Ringer's dextrose, dextrose and sodium chloride, or lactated Ringer's. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as interleukins or interferons depending on the intended use of the pharmaceutical composition.

According to a preferred embodiment of the invention said NK cells which are used for the preparation of a pharmaceutical composition for the treatment of tumors, viral or bacterial infections or inflammatory diseases are stimulated by the method according to the invention.

Further, according to the invention tumors treated with said pharmaceutical composition comprise in accordance with the invention tumor cells which express Hsp70 on the surface of their membrane. Also, cells affected by said infection or inflammation comprise in accordance with the invention cells which express Hsp70 on the surface of their membrane.

Methods for the detection of surface expression of Hsp70 are known in the art and comprise, e.g. histological methods, flow cytometry etc.

More preferred said tumors are selected from a group consisting of stomach, gastric, colorectal, pancreas, mammary, lung, gynecological, head and neck cancer, dermatological (e.g. melanoma), neuronal tumors, leukemia and lymphoma.

Preferred viral infections in accordance with the invention are infections by HIV and Hepatitis virus.

The invention also relates to the use of granzyme B for the preparation of a pharmaceutical composition for the perforin-independent treatment of tumors, viral or bacterial infections or inflammatory diseases.

A most important aspect of the present invention is mirrored by the above recited embodiment. In contrast to the speculation of the prior art, it could be shown in accordance with the present invention, that granzyme B is effective in the treatment of tumors independent of the perforin-pathway. This has important applications in the strategy of treating tumors since uptake of the pharmaceutically active compound may now be deviced independent of the perforin-pathway. Granzyme B could be administered intratumoral, iv, subcutan.

In a preferred embodiment of the use of the present invention, granzyme B is used as the only pharmaceutically active component in said pharmaceutical composition.

Again, this preferred embodiment of the invention has important implications in the design of the necessary components of the pharmaceutical composition to be used in the treatment of cancers. Importantly, there is no need to include further pharmaceutically active ingredients into the pharmaceutical composition in order to effectively treat tumors and/or reduce the size of the tumors or to treat viral or bacterial infections or inflammatory diseases.

In addition, the present invention relates to a method of treating tumor, viral or bacterial infections or inflammatory diseases comprising steps of:
(a) contacting NK-cells with tumor cells bearing Hsp70 on their surface or cells affected by said infection or inflammation amd bearing Hsp70 on their surface;
(b) allowing granzyme B to enter said cells via ion channels formed by said Hsp70 on the tumor cell surface; and
(c) allowing said cells to undergo apoptosis as a result of the enzymatic activity of granzyme B.

As an alternative, granzyme by may be directly applied instead of being expressed by stimulated NK cells. Accordingly, the present invention relates to a method of treating tumor, viral or bacterial infections or inflammatory diseases comprising steps of:
(a) contacting tumor cells bearing Hsp70 on their surface or cells affected by said infection or inflammation and bearing Hsp70 on their surface with granzyme B;
(b) allowing granzyme B to enter said cells via ion channels formed by said Hsp70 on the cell surface; and
(c) allowing said cells to undergo apoptosis as a result of the enzymatic activity of granzyme B.

Ranges of tumor cells or cells affected by said infection or inflammation and concentrations of granzyme B as well as time ranges for the contact of granzyme B and tumor cells or cells affected by said infection or inflammation can be derived from the person skilled in the art by studying the above recited teachings of the invention.

In a preferred embodiment of this method of the invention, granzyme B is administered in a final concentration of 1 μg/ml to 500 μg/ml.

In another preferred embodiment of this method of the invention, granzyme B is administered in a final concentration of 1 ng/ml to 10 ng/ml. It is most preferred that granzyme B is administered in a final concentration of about 6 ng/ml. In this regard it is important to note that modes of administration are most preferred that deliver these concentrations of granzyme B directly to the tumor cells or cells affected by said infection or inflammation.

In another preferred embodiment of the use of the present invention or the method of the present invention, granzyme B is delivered/packaged in a liposome. Encapsulation of pharmaceutically active compounds in liposomes is well established in the art.

The figures show:

FIG. 1A: Hsp70-protein (Hsp70), bovine serum albumin (BSA) and Hsp70-peptide (TKD) columns were incubated with either cell lysates of the NK-cell line YT or the non-NK cell line K562. Bound proteins were eluted from the columns in 5 fractions (F1-F5), resolved on a SDS-PAGE. Following silver stain, eluates of YT cells derived from Hsp70 and TKD columns, revealed a dominant 32 kDa protein band in fractions two (F2) and three (F3). No 32 kDa protein band was detectable in YT eluates derived from BSA columns and in K562 eluates derived from TKD columns. The position of the 32 kDa band is indicated with an arrowhead.

FIG. 1B: The tryptic peptides (SEO ID NOS:2-6) of the Coomassie-blue stained 32 kDa band of fraction 3 (F3), derived from the TKD column, correspond to human granzyme B. The probability of identification was 100% and the estimated Z-score was 1.89 corresponding to >95% confidence.

FIG. 1C: Corresponding Western blot analysis of YT and K562 cell eluates (F3) following incubation with Hsp70-protein (Hsp70) and Hsp70-peptide (TKD) columns. The blot was autoradiographed and the localization of granzyme B was visualized by immunostaining with the granzyme B specific mAb 2C5. Eluates of YT cells (left), but not of K562 cells (right) revealed a 32 kDa granzyme B protein band.

FIG. 1D: Intracellular flow cytometry of permeabilized YT cells (left) and K562 cells (right) using the phycoerythrin (PE)-conjugated granzyme B specific monoclonal antibody HC2-PE (solid line), as compared to an isotype-matched negative control antibody (dashed line). Only YT cells, but not K562 cells, contain cytoplasmic granzyme B.

FIG. 2A: Comparative binding of granzyme B (2 μg/ml) to the cell surface of CX+/Cx− and Colo+/Colo− tumor cells at 4° C., and uptake into the cytosol after a temperature shift to 37° C. for 30 min, using the phycoerythrin (PE)-conjugated granzyme B specific monoclonal antibody HC2-PE. First row, light microscopy, second row, immunofluorescence of cells without granzyme B (control); third row, immunofluorescence of cells after addition of granzyme B, as specified (grB). One representative fluorescence microscopy of three showing identical results is illustrated; magnification 40×.

FIG. 2B: Intracellular flow cytometry of permeabilized CX+/CX− (n=2) and Colo+/Colo− (n=4) tumor cells using granzyme B specific monoclonal antibody HC2-PE before (dashed line) and after (solid line) incubation of the tumor cells with 1 μg/ml, 2 μg/ml, 4 μg/ml granzyme B at 37° C. for 30 min. Only CX+ and Colo+, but not CX− and Colo− cells showed a dose-dependent shift of the granzyme B peak to the right, indicating uptake of extracellular offered granzyme B.

FIG. 3A: Percentage of Annexin V-FITC positive and propidium iodide (PI) negative CX+/Colo+ (left) and CX−/Colo− (right) cells, either untreated (black bars), or following incubation either with camptothecin (4 μg/ml; light grey bars) or granzyme B (6 ng/ml; dark grey bars) for 4 h, 12 h, and 24 h. The data represent the mean of three to four independent experiments±standard deviation; * marks values significantly different from control ($p<0.05$).

FIG. 3C: Light microscopical analysis of adherent growing CX+/CX– and Colo+/Colo– tumor cell clusters either untreated (control) or following treatment with camptothecin (cam, 4 µg/ml) or granzyme B (grB, 10 ng/ml), for 24 h. Scale bar indicates 100 µm.

FIG. 3D: In parallel, either untreated (control), camptothecin (cam) or granzyme B (grB) treated CX+/CX– and Colo+/Colo– cells (24 h) were stained with DAPI. Considerable nuclear DNA fragmentation was observed in all tumor sublines following incubation with camptothecin (middle panel). After incubation with granzyme B only CX+ and Colo+ cells exhibited nuclear DNA fragmentation (lower panel, left). No signs of apoptosis was observed in CX– and Colo– cells following incubation with granzyme B (lower panel, right). Scale bar represents 10 µm.

FIG. 4A: Light microscopy (magnification 20×) of Hsp70 membrane-positive CX+ and Hsp70 membrane-negative CX– cell colonies, either untreated (control) or following a 12 h co-incubation with Hsp70-peptide TKD stimulated NK cells (+NK). The effector to target cell ratio (E:T) was 20:1. Scale bar represents 200 µm, the insert in the lower right corner of each graph shows one representative cell colony, magnification 2.5×.

FIG. 4B: Cell kill of CX+/Colo+ (left panel) and CX–/Colo– (right panel) tumor target cells by naive (NK d0) and Hsp70-peptide TKD stimulated NK cells (NK d3) was quantified in $^{51}$Cr release assays. Intracellular granzyme B levels in naive NK cells (NK d0) versus TKD stimulated NK cells (NK d3) was 1.4-fold increased; concomitantly, lysis of CX+ cells was elevated 1.5-fold, that of Colo+ cells 2.0-fold at different effector to target ratios. Lysis of CX– and Colo– tumor cells remained unaffected.

Furthermore, the increased cytolytic activity of TKD stimulated NK cells (NK d3 Hsp70 mAb) against CX+ and Colo+ cells was completely inhibited by Hsp70 specific antibody down to the level of lysis of Hsp70 membrane-negative tumor cells (1.7-fold inhibition, dotted line). Cytotoxicity was determined at E:T ratios ranging from 2:1 to 20:1; spontaneous release of each target cell was below 10%. The data represent the mean of three independent experiments±standard deviation.

EXAMPLES

The following examples illustrate the invention. These examples should not be construed as limiting: the examples are included for purposes of illustration and the present invention is limited only by the claims.

Example 1

Materials and Methods

Cells

The NK cell line YT was cultured at cell densities ranging from 0.1-0.5×10$^6$ cells/ml RPMI-1640 medium (Life Technologies, Eggenstein, Germany) containing 10% heat inactivated fetal calf serum (FCS, Life Technologies, Eggenstein, Germany) supplemented with 6 mM L-glutamine, and antibiotics (100 IU/ml penicillin and 100 µg/ml streptomycin; Life Technologies). Transient plastic adherent NK cells were derived from buffy coats of healthy human volunteers. Ficoll separated peripheral blood mononuclear cells (PBMC) were cultured in rIL-2 (100 IU/ml, Chiron, Frankfurt, Germany) for 12 h. Following adherence selection of monocyte depleted peripheral blood lymphocytes according to a modified method of Vujanovic (Vujanovic et. al. (1993) Cell. Immunol. 151, 133), cells were cultivated in RPMI-1640 medium supplemented with Hsp70-peptide TKD (2 µg/ml) for 3 days. The human tumor sublines CX+/CX– and Colo+/Colo– were derived by cell sorting of CX-2 colon (Hsp70 positive: 60%) and Colo357 pancreas (Hsp70 positive: 70%) carcinoma cell lines using the Hsp70 specific monoclonal antibody C92F3B1, according to a previously described protocol (Multhoff et. al. (1997) J. Immunol. 158, 4341). Consequently, CX+ and CX– are autologous, as are Colo+ and Colo– Hsp70 stably high expressing CX+ (Hsp70 positive: 80%) and Colo+ (Hsp70 positive: 85%) carcinoma sublines differ significantly from Hsp70 stably low expressing CX– (Hsp70 positive: 25%) and Colo– (Hsp70 positive: 35%) carcinoma cells.

The carcinoma sublines CX+/Colo+ and CX–/Colo–, that differ with respect to their membrane expression of Hsp70, but exhibit identical MHC class I expression, and the leukemic non-NK cell line K562 were cultured in RPMI-1640 medium supplemented with 5% FCS, 6 mM L-glutamine and antibiotics. Exponentially growing tumor cells (day 1 after cell passage) were used for granzyme B, camptothecin treatment and as targets in cytotoxicity assays.

All cell lines were screened regularly for mycoplasma contaminations by an enzyme-immunoassay detecting *M. arginini, M. hyorhinis A. laidlawii*, and *M. orale* (Roche, Mannheim, Germany). Only mycoplasma-free cell lines were used.

Affinity Chromatography and Immunoprecipitation

Bovine serum albumine (BSA, 1 mg/ml, Sigma-Aldrich, Steinheim, Germany), 1 mg/ml lyophylized, recombinant human Hsp70-protein (Stressgen, British Columbia, Canada) or 2 mg/mi Hsp70-peptide TKD (TKDNNLLGRFELSG (SEO ID NO:1), aa$_{450-463}$, Bachem, Bubendorf, Switzerland) were incubated with equilibrated AminoLink agarose beads (Pierce, Rockford, USA) in 2 ml for 6 h, together with the reductant NaCNBH$_3$. Binding capacity of BSA, Hsp70-protein and Hsp70-peptide TKD was greater 95%. Following removal of uncoupled material by extensive washing with Tris-buffer and quenching of non-reactive groups, cell lysates were administered to the BSA, Hsp70-protein and Hsp70-peptide TKD conjugated columns for 1 h.

After washing with 10 column volumes of 20 mM Tris buffer, bound proteins were eluted with 3 M sodium chloride in 20 mM Tris buffer, in 5 fractions. Each fraction was subjected to a 10% SDS-PAGE and blotted to PVDF membranes.

Membrane Preparation

Membrane purification was performed by dounce homogenization of 50×10$^6$ cells in hypotonic, EDTA-free buffer containing the protease inhibitor PMSF followed by sequential centrifugation at 1,000 g for 5 min and at 100,000 g, at 4° C., for 60 min. The pellet containing membranes was resuspended in 2 ml 0.3 M NaCl in 50 mM Tris buffer, 0.5% NP40, pH 7.6.

Western Blot Analysis

Following blocking in skim-milk (0.1%) and incubation with mAb directed against granzyme B 2C5 (IgG2a, Becton Dickinson, Heidelberg, Germany), at 4° C., for 5 h, Western blots were washed and incubated with a secondary mouse anti-IgG HRP Ab (Dianova, Hamburg, Germany), for 1 h. Proteins were detected using the ECL kit (Amersham Bioscience) for 5 sec.

Protein Identification by Peptide Mass Fingerprinting

The Hsp70-protein and Hsp70-peptide TKD precipitated 32 kDa protein band was cut out from Coomassie-blue stained gels, digested with trypsin, and desalted using reversed phase ZIP tips (Millipore, Eschborn, Germany. The samples were embedded in 4-hydroxy-α-cyano-cinnamic acid and the peptide masses were determined with a Perseptive Voyager DePro MALDI-TOF (Matrix Assisted Laser Desorption Ionisation—Time Of Flight) mass spectrometer in reflective mode. A peaklist was compiled with the m/z software (Proteometrics) and used for peak selection; the resulting peptide mass fingerprint was used to search the non-redundant NCBI protein database using the Profound search engine (Proteometrics). Granzyme B was identified with 100% probability and >95% confidence.

Flow Cytometry

Cells ($0.5 \times 10^6$) were fixed in paraformaldehyde (1% PFA in PBS) for 10 min, and permeabilized in PBS containing BSA (0.5%), $NaN_3$ (0.1%), and saponin (0.1%). Then permeabilized cells were incubated either with the granzyme B-phycoerythrin conjugated monoclonal antibody HC2-PE (IgG1; Hölzel Diagnosbka, Cologne, Germany) with an isotype-matched IgG1 control antibody, at 4° C. for 1 h, in the dark. Following washing cells were analysed on a FACSCalibur instrument (Becton Dickinson, Heidelberg, Germany).

Treatment

Stock solutions of camptothecin (4 mg/ml, Sigma, Munich, Germany) were diluted in DMSO and stored at 4° C. in the dark. Granzyme B (6 ng/ml, Hölzel Diagnostics, Cologne, Germany) solutions were freshly prepared directly before usage. Exponentially growing cells ($0.5-1.5 \times 10^6$/ml) were incubated either with camptothecin at a final concentration of 4 µg/ml or with purified, enzymatically active granzyme B (10 ng/ml, 1 µg/ml, 2 µg/ml; 4 µg/ml) (Shi et. al. (2000) Methods in Enzymology 322, 125) for 10 min, and 30 min either at 4° C. or at 37° C. After washing in RPMI-1640 medium binding and uptake was determined in nonpermeabilized and permeabilized tumor cells by flow cytometry and fluorescence microscopy on a Axioscop 25 scanning microscope (Zeiss, Jena, Germany) equipped with a 40× objective and standard filters. Images were treated by multiplicative shading correction using the software Axiovison (Zeiss Vison, Jena, Germany). Granzyme B was visualized in red by using the HC2-PE antibody.

Apoptotic Cell Death was Determined after Incubation of Tumor Cells with 6 ng/ml Granzyme B for 4 h, 12 h, and 24 h at 37° C. and Washing in RPMI-1640 Medium by Different Apoptosis Assays, as Described Below. Apoptosis Assays Annexin V-FITC staining: Briefly, cells were washed twice in Hepes buffer containing 5 mM $CaCl_2$ and incubated with Annexin V-FITC (Roche) for 10 min at room temperature. Annexin V-FITC positively stained cells were measured on a FACSCalibur flow cytometer (Becton Dickinson, Heidelberg, Germany).

DAPI-staining: Methanol/aceton fixed cells ($0.1 \times 10^6$ cells/100 µl) were incubated with 0.5 µg/µl 4,6-diamino-2-phenylindole (DAPI) in PBS/glycerol (3:1), for 15 min in the dark. Following washing in PBS the cells were mounted with Fluorescent Mounting Medium (Dako, Glostrup, Denmark) and than analysed for fluorescence using a Zeiss model Axioscop 2 scanning microscope (Zeiss Jena, Germany) equipped with a 40× objective and standard filters. Apoptosis was visualized with DAPI-staining in 50 cells, each. Images were treated by multiplicative shading correction using software Axiovision (Zeiss Vision Jena, Germany).

Cytochrome c release: Cytochrome c release was determined using a quantitative immunoassay; (DCDCO, R&D Systems, Wiesbaden, Germany). Briefly, either untreated, camptothecin (4 µg/ml) or granzyme B (6 ng/ml) treated CX+ and CX− cells ($1.5 \times 10^6$/ml) were washed in PBS and treated with lysis buffer for 1 h at room temperature. Following centrifugation at 1,000 g for 15 min supernatants were removed and 200 µl of a 1:100, 1:250, and a 1:500 dilution was used for a sandwich ELISA. Following incubation with substrate solution in the dark for 30 min the reaction was stopped. The optical density of each well was determined on an ELISA reader at 450 nm. The amount of cytochrome c was determined according to a calibration curve.

Granzyme B ELISPOT

Granzyme B release was compared in unstimualted NK cells (NK d0) and TKD stimulated NK cells (NK d3) after a 4 h co-incubation period with tumor cell lines CX+/CX− and Colo+/Colo−, at different effector to target cell ratios (E:T) ranging from 20:1 to 2:1. For detection a Granzyme B ELISPOT kit (#552572, BD, Heidelberg, Germany) was used. Briefly, 96-well ELISPOT plates (MAIPN45, Millipore) were coated overnight at 4° C. with capture antibody, blocked with RPMI-1640 culture medium containing 10% FCS and incubated with tumor and effector cells for 4 h at 37° C., as specified before. After washing in deionized water and wash buffers A and B, biotinylated anti-granzyme B antibody was added (2 µg/ml) for 2 h. After another two washing steps granzyme B was visualized by the addition of freshly prepared avidin-horseradish peroxidase (2 h) and substrate solution (25 min incubation period). Spots were counted automatically using ImmunoSpot Series I Analyzer. $^{51}$Cr Release Assay and Inhibition Assay NK cell mediated cytotoxicity was measured using a 12 h $^{51}$Cr radioisotope assay. As target cells the colon carcinoma sublines CX+ and CX− were used. For blocking studies the mAb C92F3B1 and an isotype matched control antibody (IgG1) were used at a final concentration of 5 µg/$1 \times 10^6$ cells. Following incubation of CX+ and CX− target cells with the antibodies for 30 min at 4° C., the cells were labeled with $^{51}$Cr and the cytotoxicity assay was performed as described by MacDonald (MacDonald et. al. (1974) J. Exp. Med. 140,718). The percentage of specific lysis was calculated as: [(experimental release−spontaneous release)/(maximal release−spontaneous release)]×100.

Example 2

Figure 1:
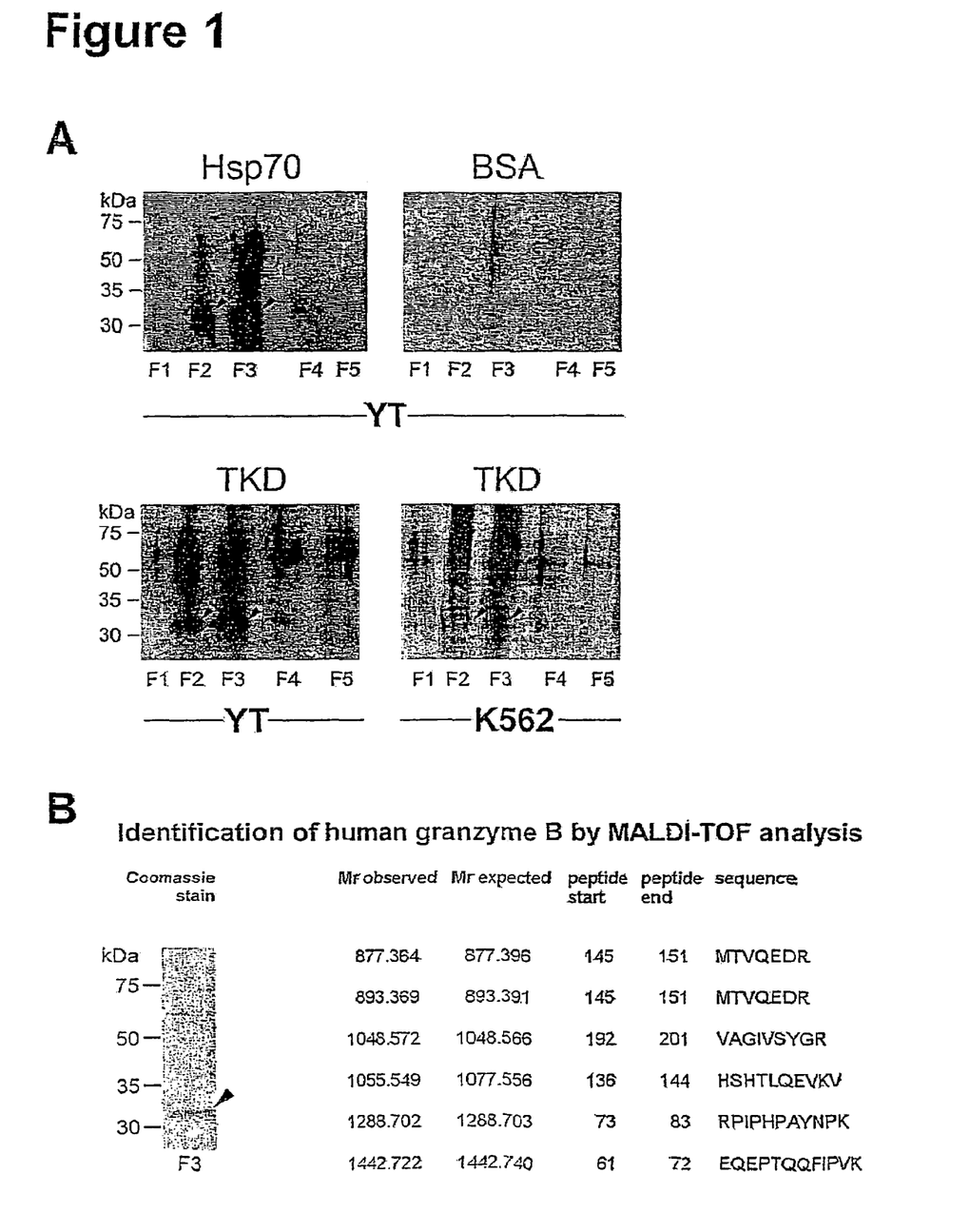
FIG. 1 shows the identification of granzyme B as the interacting partner for Hsp70-protein and Hsp70-peptide TKD.

Granzyme B is an Interacting Partner of Full Length Heat Shock Protein 70 (Hsp70) and of Hsp70-peptide TKD Partner proteins were identified by affinity chromatography on immobilized human Hsp70-protein (1 mg) or a 14 amino acid peptide, coined TKD (TKDNNLLGRFELSG, $aa_{450-463}$, 2 mg), containing the extracellular epitope of Hsp70 that was found mediating the interaction with NK cells. This peptide was previously identified as the epitope (Reineke et. al. (1-996) Immunobiol. 196, 96) of an Hsp70 specific antibody (Welch and Suhan (1986) J. Cell. Biol. 103, 2035), which specifically detects membrane-bound Hsp70 on viable tumor cells (Multhoff et. al. (1995) Int. J. Cancer 61,272; Multhoff et. al. (1995) Blood 86,1374). A cell lysate of the NK cell line YT (Drexler et. al. (2000) Leukemia 14,777) was fractionated on immobilized Hsp70 or TKD peptide columns. The material bound to the columns was eluted with 3 M sodium chloride within five fractions. As controls, YT cell lysates were administered to carrier or BSA-conjugated columns. Moreover, lysate of a non-NK cell line (K562) was fractionated on TKD-conjugated affinity column. The eluted fractions were separated by SDS-PAGE (10%) and visualized by silver-staining. A dominant protein band of apparent molecular weight of 32 kDa was observed in fractions two (F2) and three (F3) of YT cell eluates derived from the Hsp70-protein (Hsp70) and the Hsp70-peptide (TKD) column (FIG. 1A, YT). This band was not observed in eluates of unconjugated sepharose columns (data not shown) or BSA-conjugated colums nor in the material eluted from the TKD affinity columns loaded with K562 cell lysates (FIG. 1A,). Identical results were obtained with Hsp70-protein columns (data not shown). In parallel, the eluates of Hsp70-peptide TKD and Hsp70-protein derived from fraction 3 (F3) were separated by SDS-PAGE and stained with Coomassie-blue. The 32 kDa protein band derived from F3 of the Hsp70-peptide column was cut out and digested with trypsin (FIG. 1B). The resulting peptides were analyzed by MALDI-TOF peptide mass fingerprinting. Sequence of the tryptic peptides exhibited 100% homology with granzyme B with an estimated Z-value was 1.89 indicating a probability of greater 95% for granzyme B (FIG. 1B). The identity of the 32 kDa protein band as granzyme B was further confirmed by Western blot analysis using the granzyme B specific antibody 2C5 (IgG2a): YT cell eluates obtained from Hsp70-protein (Hsp70) and Hsp70-peptide (TKD) columns, both revealed a dominant 32 kDa granzyme B protein band (FIG. 1C). Granzyme B was not detected in eluted fraction of Hsp70 or TKD affinity columns loaded with K562 cell lysates (FIG. 1C). Flow cytometry using a phycoerythrin (PE)-conjugated granzyme B antibody (IgG1) again granzyme B showed positive staining for cytoplasmic granzyme B in YT cells, but not K562 cells (FIG. 1D). These observations corroborate our previous results. In summary, these data indicate granzyme B is a potential partner protein of Hsp70. Granzyme B is likely to interact with the C-terminal region of Hsp70 termed TKD.

Example 3

Figure 2:
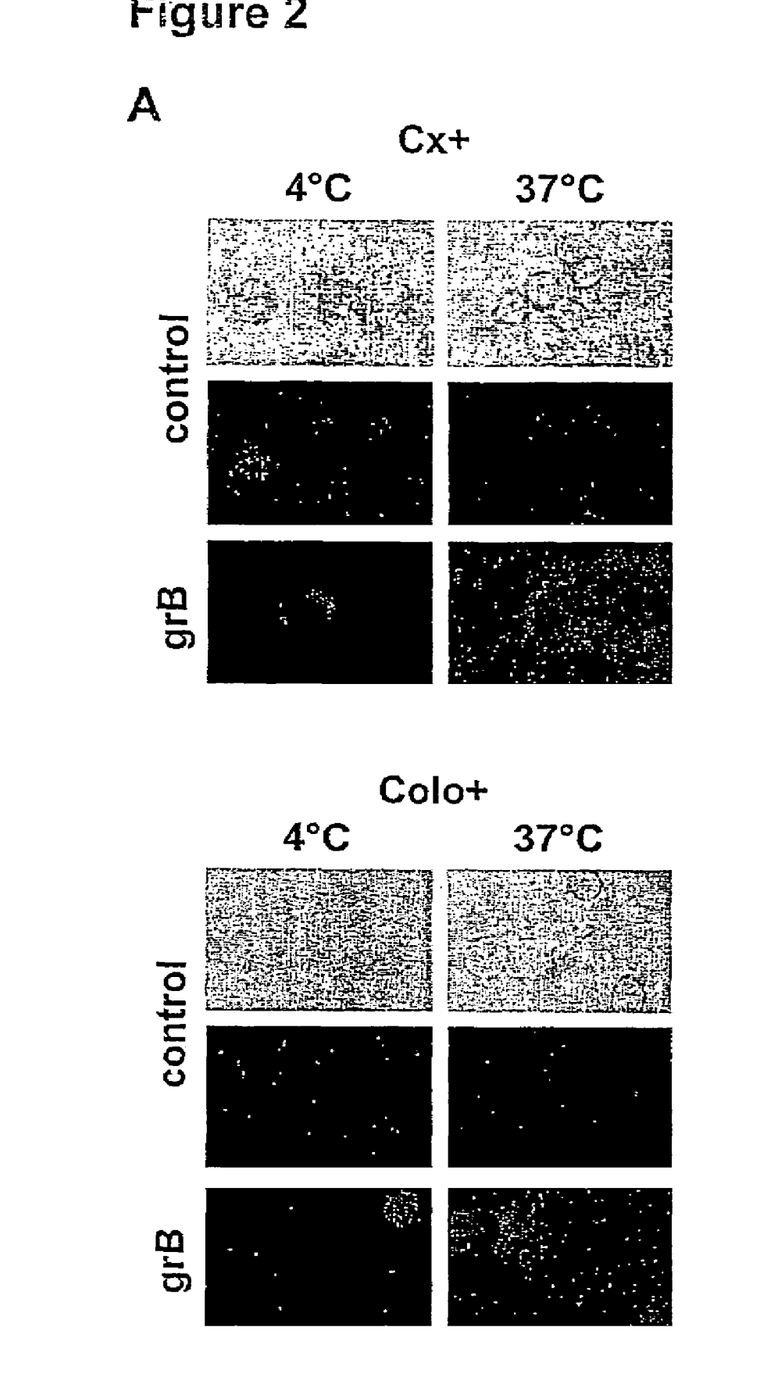
FIG. 2 shows specific cell surface binding and uptake of granzyme B (grB) by Hsp70 membrane-positive tumor cells

Specific Binding and Internalization of Granzyme B in Hsp70 Membrane-Positive Tumor Cells The preceding findings posed the question whether membrane-bound Hsp70 might enable specific binding and entry of granzyme B into the cytosol. Therefore, perforin-free, purified granzyme B was co-incubated with tumor cell sublines CX+/CX− and Colo+/Colo− that exhibit differential Hsp70 membrane expression. A light microscopical analysis of untreated CX+ and Colo+ cells (control) at 4° C. versus 37° C. is shown in the upper row of each panel (FIG. 2A). The corresponding immunofluorescence microscopy of the cells at 4° C. and 37° C. is illustrated below (control). Initially, none of the cells showed any granzyme B staining, neither on the cell surface nor in the cytoplasm. However, after a 15 min incubation period of the cells with purified granzyme B (gr B) at 4° C., a ring-shaped fluorescence, indicating a typical cell surface staining, was detected on Hsp70 membrane-positive CX+ and Colo+ tumor sublines (FIG. 2A, left panel). A temperature shift from 4° C. to 37° C. during the 30 min incubation period resulted in uptake of granzyme B, as determined by a cytoplasmic staining pattern in CX+ and Colo+ tumor sublines (FIG. 2A, right panel). In contrast, the Hsp70 membrane-negative counterparts CX− and Colon− either exhibited any granzyme B cell surface binding at 4° C. nor uptake at 37° C. (data not shown). Flow cytometry analysis of permeabilized cells revealed a faint shift of the granzyme B peak to the right selectively in Hsp70 membrane-positive CX+ and Colo+, but not in CX− and Colo− tumor sublines, if the cells were co-incubated with 1 µg/ml granzyme B for 30 min at 37° C. (FIG. 2B, upper graph). A dose-dependent increase in granzyme B uptake, in Hsp70 membrane-positive tumor cells (CX+/Colo+) was detected after co-incubation with 2 µg/ml and 4 µg/ml granzyme B (FIG. 2B, lower graph). However, even at the highest concentration of 4 µg/ml, granzyme B was internalized much more pronounced by Hsp70 membrane-positive as compared to Hsp70-negative tumor cells (CX−/Colo−). Potential ion channels formed by Hsp70 may play a role in the mechansim of selective granzyme B uptake in Hsp70 membrane-positive tumor cells. Indeed, a particular ion conductance pathway was observed after incorporation of vesicles derived from purified phospholipids of Hsp70 membrane-positive (CX+) tumor sublines. This was not seen in vesicles obtained from Hsp70 membrane-negative (CX−) tumor cells (data not shown). Based on these results one might speculate about an ion channel activity facilitating uptake of granzyme B, selectively into Hsp70 membrane-positive tumor cells.

Example 4

Figure 3:
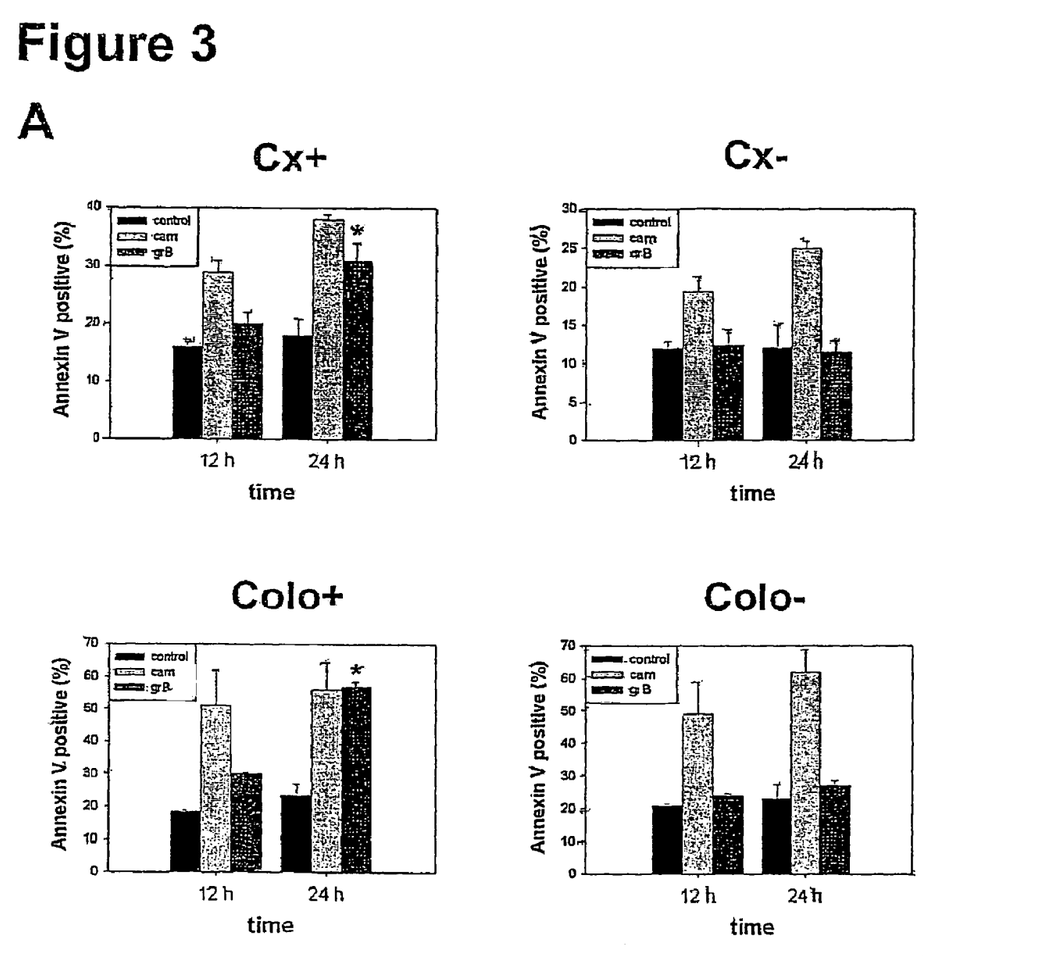
FIG. 3 shows an experiment in which apoptosis is selectively induced by isolated granzyme B (grB) in Hsp70 membrane-positive tumor cells

In vitro Provided Granzyme B Induces Apoptosis Selectively in Hsp70 Membrane-Positive Tumor Cells The preceding findings posed the question whether purified granzyme B can induce apoptosis of tumor cells that present Hsp70 on their cell surface. Hsp70 membrane-positive (CX+/Colo+) and negative (CX−/Colo−) colon carcinoma cells, that exhibit an identical MHC class I expression (Multhoff et. al. (1997) J. Immunol. 158,4341), were incubated for 4 h, 12 h, and 24 h with isolated enzymatically active granzyme B (6 ng/ml) (Shi et. al. (2000) Methods in Enzymology 322, 125). As a positive control for apoptosis all cell types were incubated with the topoisomerase inhibitor camptothecin at a concentration of 4 µg/ml. Apoptosis was determined by Annexin V-FITC staining measured by FACS (FACSCalibur, Becton Dickinson, Heidelberg, Germany), DAPI staining and mitochondrial cytochrome c release. Apoptosis was not detected in CX+ and CX− cells incubated with camptothecin (cam) or granzyme B (grB) for 4 h incubation (FIG. 3A). CX+ and Colo+ as well as CX− and Colo− cells incubated with camptothecin underwent apoptosis after a 12 h and 24 h incubation period with camptothecin. It appeared that the colon carcinoma sublines CX+/CX− are better protected towards a camptothecin-mediated cell death as compared to the pancreas carcinoma sublines Colo+/Colo−.

Figure 3B:
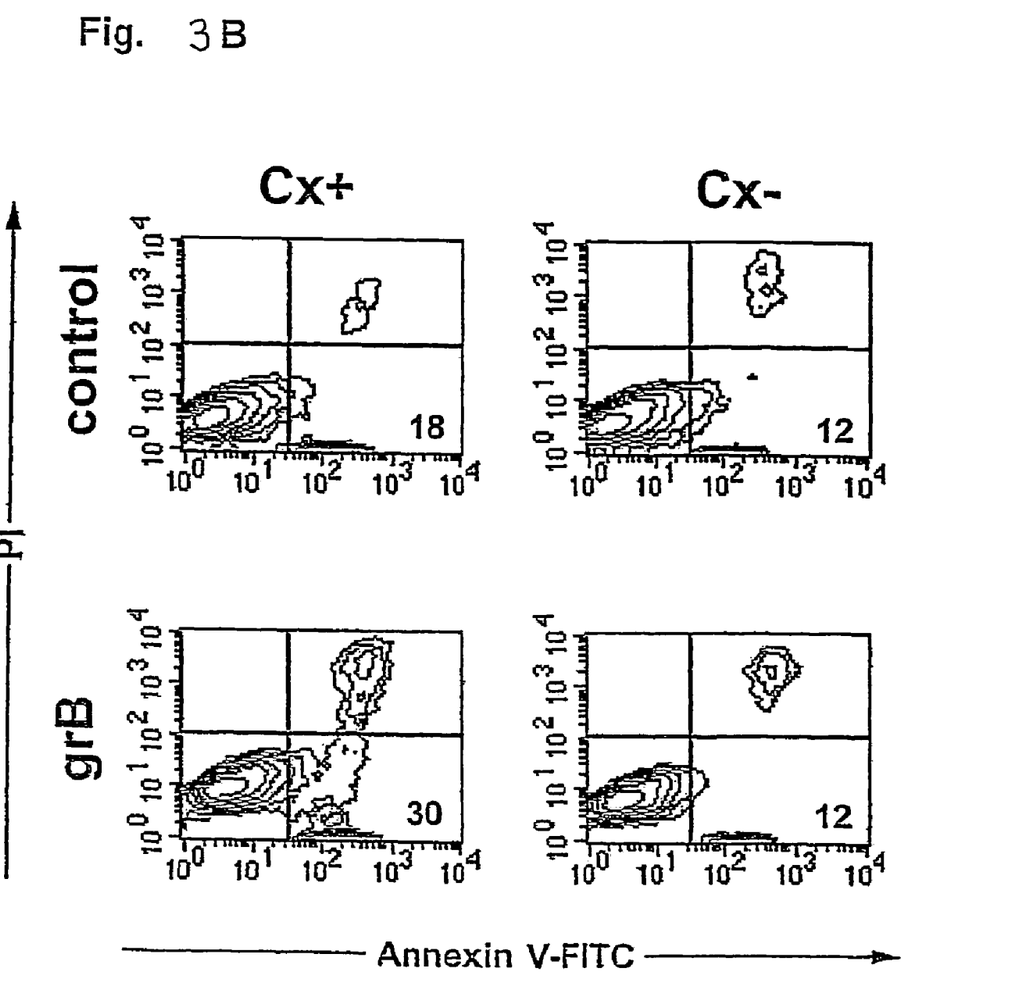
FIG. 3B: A representative flow cytometric analysis of Annexin V-FITC positively and propidium iodide (PI) negatively stained CX+ and CX– cells, either untreated (control), or following incubation with granzyme B (grB) for 24 h. The percentage of Annexin V-FITC positively stained cells is given in percentage in the lower right corner of each graph.

As shown in FIG. 3A, after 12 h the amount of Annexin V-FITC positively stained CX+ cells increased from 16.6% to 28.0% (1.7-fold) and after 24 h from 18% to 39% (2.1-fold). In CX− cells the amount of Annexin V-FITC positively stained cells increased similarly from 12.1% to 19.8% (1.6-fold) after 12 h, and from 11.9% to 25.1% (2.1-fold) after 24 h. In contrast, apoptosis was observed selectively in Hsp70 membrane-positive CX+ cells, incubated with granzyme B for 12 h and 24 h, with an increase of 16.6% to 20.9% (1.3-fold), and of 18% to 30.2% (1.8-fold), respectively. Similarly, a 1.3-fold and a 2.4-fold increase in the amount of Annexin V-FITC positively stained Colo+ cells were observed after 12 h and 24 h, respectively. In CX− and Colo− cells neither a 12 h nor a 24 h treatment with granzyme B induces apoptosis. A comparative Annexin V-FITC staining pattern of CX+ and CX− cells treated with granzyme B for 24 h, is illustrated in FIG. 3B. Compared to untreated control cells (18%), the amount of Annexin V-FITC positively and propidium iodide (PI) negatively stained CX+ cells increased 1.7-fold (30%) following treatment with granzyme B. However, the amount of apoptotic CX− cells remained unaltered before and after identical treatment with granzyme B. In addition to CX+ cells, granzyme B induces apoptosis also in the Hsp70 membrane-positive leukemic cell line K562 (data not shown). The amount of Annexin V-FITC positively stained K562 cells increased from 8.7% up to 16% (1.8-fold).

In order to exclude apoptosis initiated by anoikes light microscopical analysis of untreated (control), camptothecin (cam) and granzyme B (grB) treated CX+/CX− and Colo+/Colo− tumor cells were performed. As shown in FIG. 3C, 24 h post-treatment with granzyme B, neither Hsp70 membrane-positive nor -negative tumor cell lines exhibited any signs of loss in plastic adherence. Regarding these findings we ruled out the possibility that anoikes might be a possible mechanism for the induction of apoptotic cell death in Hsp70 membrane-positive tumor sublines. It is important to note that all apoptosis assays were determined within the adherent cell population following a short term (<1 min) trypsinization.

Consistent with the results from Annexin V-FITC staining pattern all cell types, CX+/CX−, Colo+/Colo− exhibited nuclear fragmentation, a typical sign of apoptosis at a later stage, as detected by DAPI-staining of nuclear DNA following treatment with camptothecin (4 μg/ml) for 24 h (FIG. 3D, cam). However, DNA fragmentation was detected only in Hsp70 membrane-positive CX+ and Colo+ tumor cells after 24 h of granzyme B treatment (6 ng/ml), whereas no DNA fragmentation was observed in Hsp70 membrane-negative CX− and Colo− cells (FIG. 3D, grB).

As an additional test for apoptotic cell death, cytochrome c release was measured following incubation of CX+ and CX− cells with granzyme B for 24 h. As summarized in Table I, following incubation with granzyme B (6 ng/ml) for 24 h, cytochrome c concentration was elevated from 0.382 mg/ml to 0.690 mg/ml (1.8-fold) in CX+ cells. However, no increase in cytochrome c was observed in CX− cells following treatment with granzyme B (0.452 mg/ml versus 0.425 mg/ml). In contrast, an incubation with camptothecin (4 pg/ml) for 24 h, results in a comparable 1.5-fold increase in cytochrome c concentrations in both cell types. These results indicate that isolated granzyme B induces apoptotic cell death selectively in tumor cells presenting Hsp70 on their cell surface. It was propose that the trigger of apoptosis by granzyme B is mediated via the extracellular exposed Hsp70 epitope TKD.

TABLE I

Quantitative determination of human cytochrome c in CX+ and CX− tumor cells either untreated (control), or following incubation with camptothecin (4 μg/ml) or granzyme B (6 ng/ml) for 24 h. The data represent the mean of 4 independent experiments ± S.E.; *marks values significantly different from control ($p < 0.05$).

| cells | cytochrome c (mg/ml) fold increase | | |
|---|---|---|---|
| | control | camptothecin | granzyme B |
| CX+ | 0.382 ± 0.02 | 0.555 ± 0.04* | 0.690 ± 0.08* |
| | 1.0 | 1.5 | 1.8 |
| CX− | 0.452 ± 0.02 | 0.672 ± 0.02* | 0.425 ± 0.075 |
| | 1.0 | 1.5 | 0.9 |

Example 5

Figure 4:
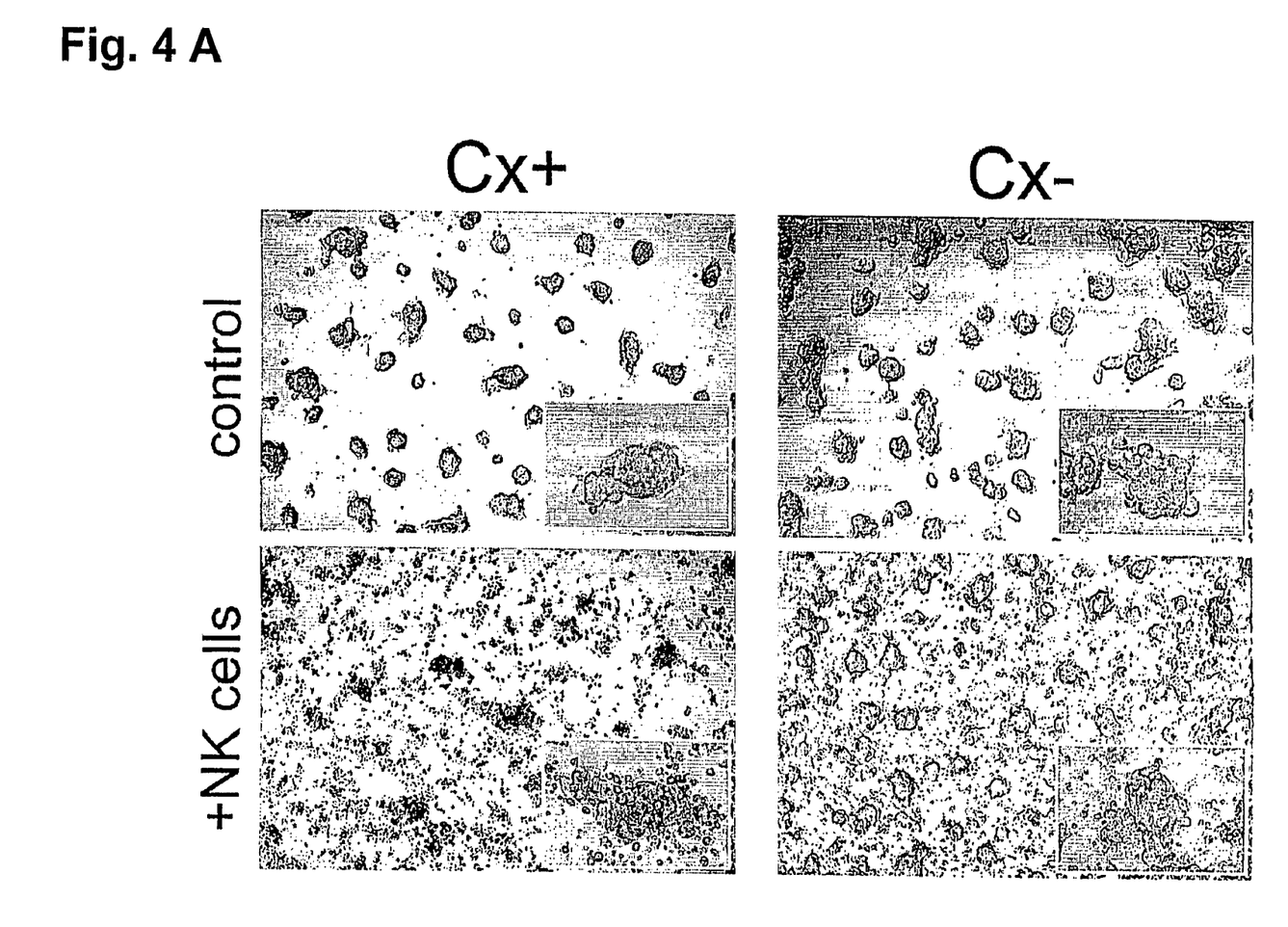
FIG. 4 shows an experiment in which kill of Hsp70 membrane-positive tumor cells is demonstrated. Apoptosis mediated by granzyme B positive NK cells is blockable by Hsp70 specific mAb.

Stimulation of NK Cells with Hsp70-peptide TKD Induces the Production of Granzyme B and Increases Kill of Hsp70 Membrane-Positive Tumor Target Cells The physiological role of our findings was tested in functional assays using naive and Hsp70 stimulated human NK cells. Previously, it was shown that incubation of NK cells with Hsp70-protein at concentrations between 10 and 50 μg/ml or with equivalent Hsp70-peptide concentrations (0.2-2.0 μg/ml) resulted in increased cytolytic activity of NK cells against Hsp70 membrane-positive tumor target cells. Concomitantly, the expression of the killer cell activating C-type lectin receptor CD94 was upregulated (Multhoff et. al. (1999) Exp. Hematology 27,1627; Gross et. al. (2002) submitted). Although Hsp70 acts as a tumor-selective recognition structure for NK cells, as determined by antibody blocking studies (Multhoff et. al. (1997) J. Immunol. 158,4341; Multhoff et. al. (1995) Blood 86,1374), the NK-cytotoxic mechanism remains unclear. To elucidate the possible mechanism, NK cells were incubated with Hsp70-peptide TKD (2 pg/ml) for 3 days. A significantly elevated intracellular granzyme B expression, as determined in 3 independent experiments, was observed. In contrast, granzyme B expression was not increased in CD3 positive T cells treated with Hsp70-peptide TKD. Light microscopical analysis of Hsp70-peptide activated NK cells co-incubated with Hsp70 membrane-positive CX+ and Hsp70 membrane-negative CX− cells is illustrated in FIG. 4A. Hsp70 membrane-positive CX+ and Hsp70 membrane-negative CX− tumor cells ($0.1 \times 10^6$ cells/ml) were cultured in duplicates in 24 well plates for 2 days. The proliferation rate of both tumor cell lines was comparable, as determined by identical cell counts ($0.3 \times 10^6$ cells/ml). CX+ and CX− tumor cells in the upper panel were cultured in the absence of NK cells; tumor cells in the lower panel were co-cultured for 12 h with NK cells that had been stimulated with Hsp70-peptide TKD (2 μg/ml, 3 days). Nearly 100% of the CX+ cell colonies were found in clusters with NK cells and viability of CX+ tumor cells appears to be reduced. In contrast, CX− tumor cells and NK cells were not found in clusters; Hsp70 membrane-negative CX− tumor cells did not attract NK cells. Cell viability of CX− tumor cells following contact with NK cells appears to be less affected, as compared to that of CX+ tumor cells. The inserts in the lower right corner of each graph illustrates a 2.5× magnification of one representative cell colony.

Cell kill of CX+/CX− and Colo+/Colo− tumor cells following contact with freshly isolated, unstimulated (NK d0) or Hsp70-peptide TKD stimulated NK cells (NK d3) was quantitated in a 12 h $^{51}$Cr release assay (FIG. 4B). Consistently with what was observed in light microscopy (FIG. 4A), the cytolytic activity of TKD stimulated NK cells (NK d3) against CX+ target cells (left) was significantly enhanced as compared to CX− target cells (right). Concomitant with the increased granzyme B levels following stimulation with Hsp70-peptide TKD for 3 days, the cytolytic response against Hsp70 membrane-positive CX+ and Colo+ cells, but not against Hsp70 membrane-negative CX− and Colo− cells was significantly elevated; 1.5-fold (CX+) and 2.0-fold (Colo+) at E:T ratios of 2:1 to 20:1. Since CX+ and CX− tumor cells differ only with respect to their Hsp70 membrane expression but exhibit an identical MHC class I expression pattern the inhibitory effect mediated by killer cell inhibitory receptors (KIR) could be excluded. The increased cytolytic activity against. Hsp70 membrane-positive CX+ tumor cells (left), but not against Hsp70 membrane-negative CX− tumor cells (right), could be completely inhibited by pre-incubation of the target cells with the Hsp70 specific monoclonal antibody that is known to detect membrane-bound Hsp70-peptide TKD on viable tumor cells (Multhoff et. al. (1995) Int. J. Cancer 61, 272). In contrast, the lower lysis of Hsp70 membrane-negative tumor cells remained unaffected after incubation with Hsp70 antibody. Technically, it is not possible to quantify the absolute amount of granzyme B that is transferred from NK cells into tumor cells by cell-to-cell contact. However, relative values of granzyme B release could be determined by ELISPOT analysis. Therefore, a comparison of the cytolytic response of freshly isolated, unstimulated (NK d0) and TKD-stimulated NK cells (NK d3) against CX+/CX− and Colo+/Colo− tumor cells was performed concomitantly with the definition of the granzyme B release. Irrespectively of the tumor cell line and the E:T cell ratio, co-incubation of tumor cells with unstimulated NK cells (NK d0), always results in very low granzyme B release; the number of spots was always less than 20. After a 3 day stimulation period with TKD (NK d3) followed by a 4 h coincubation time with tumor cells, granzyme B release was significantly upregulated. At an E:T ratio of 5:1, the number of granzyme B spots, as determined in three independent experiments, was as follows: CX+ 260±20, CX− 165±6; Colo+ 137±55; Colo− 66±8. Concomitantly, Hsp70 membrane-positive tumor target cells (CX+/Colo+), were lysed significantly better as compared to their-negative counterparts (CX−/Colo−). These data strongly suggest that lysis of Hsp70 membrane-positive tumor cells by TKD-activated NK cells is associated with granzyme B release. It was hypothesized that interaction of granzyme B with membrane-bound Hsp70-peptide TKD is key for its uptake into tumor cells and for the induction of apoptosis. When NK cells were removed by washing with PBS and the tumor cells were stained with DAPI. Hsp70 membrane-positive CX+ cells showed DNA fragmentation, whereas Hsp70 membrane-negative CX− cells not following co-incubation with NK cells. Identical results were obtained with Annexin V-FITC staining (data not shown). These observations strongly suggests that TKD activated NK cells kill Hsp70 membrane-positive CX+ cells by induction of apoptosis, which also have elevated levels of granzyme B.

The invention claimed is:

1. A method of treating a tumor comprising tumor cells which express Hsp70 on their cell surface, said method comprising:
   (a) administering a pharmaceutical composition consisting essentially of a pharmaceutically effective amount of isolated granzyme B as the only pharmaceutically active component to tumor cells, said tumor cells bearing Hsp70 on their surface;
   (b) allowing granzyme B to enter said cells via Hsp70 on the surface of said cells; and
   (c) allowing said cells to undergo apoptosis as a result of the enzymatic activity of granzyme B.

2. The method of claim 1, wherein granzyme B is present in the pharmaceutical composition in a final concentration of 1 µg/ml to 500 µg/ml.

3. The method of claim 1, wherein granzyme B is present in the pharmaceutical composition in a final concentration of 1 ng/ml to 10 ng/ml.

4. The method of claim 3 wherein granzyme B is present in the pharmaceutical composition in a final concentration of about 6 ng/ml.

5. A method of treating a tumor comprising tumor cells which express Hsp70 on their cell surface, said method comprising:
   (a) analyzing tumor cells of a patient for surface expression of Hsp70;
   (b) administering a pharmaceutical composition comprising a pharmaceutically effective amount of granzyme B to said tumor cells, said cells bearing Hsp70 on their surface;
   (c) allowing granzyme B to enter said cells via Hsp70 on the cell surface; and
   (d) allowing said cells to undergo apoptosis as a result of the enzymatic activity of granzyme B.

6. The method of claim 5, wherein granzyme B is present in the pharmaceutical composition in a final concentration of 1 µg/ml to 500 µg/ml.

7. The method of claim 5, wherein granzyme B is present in the pharmaceutical composition in a final concentration of 1 ng/ml to 10 ng/ml.

8. The method of claim 7 wherein granzyme B is present in the pharmaceutical composition in a final concentration of about 6 ng/ml.

* * * * *